(12) United States Patent
Goble

(10) Patent No.: US 6,994,725 B1
(45) Date of Patent: Feb. 7, 2006

(54) METHOD AND APPARATUS FOR RECONSTRUCTING A LIGAMENT

(75) Inventor: E. Marlowe Goble, Alta, WY (US)

(73) Assignee: Medicinelodge, Inc., Logan, UT (US)

( * ) Notice: Subject to any disclaimer, the term of this patent is extended or adjusted under 35 U.S.C. 154(b) by 0 days.

(21) Appl. No.: 09/970,559

(22) Filed: Oct. 3, 2001

Related U.S. Application Data

(60) Provisional application No. 60/237,817, filed on Oct. 3, 2000.

(51) Int. Cl.
*A61F 2/08* (2006.01)

(52) U.S. Cl. ................ 623/13.14; 623/13.13; 606/72; 606/232

(58) Field of Classification Search .. 623/13.11–13.14; 606/72, 73, 232
See application file for complete search history.

(56) References Cited

U.S. PATENT DOCUMENTS

| | | | | |
|---|---|---|---|---|
| 4,773,910 A | * | 9/1988 | Chen et al. ............... 623/13.2 |
| 4,927,421 A | * | 5/1990 | Goble et al. ................ 606/73 |
| 4,950,270 A | * | 8/1990 | Bowman et al. ............. 606/72 |
| 5,456,721 A | * | 10/1995 | Legrand .................. 623/13.15 |
| 5,584,835 A | * | 12/1996 | Greenfield .................. 606/73 |
| 5,674,224 A | * | 10/1997 | Howell et al. ............... 606/88 |
| 5,688,284 A | * | 11/1997 | Chervitz et al. ............. 606/96 |
| 5,702,397 A | * | 12/1997 | Goble et al. ................ 606/72 |
| 5,766,250 A | * | 6/1998 | Chervitz et al. ............. 606/72 |
| 6,066,173 A | * | 5/2000 | McKernan et al. ...... 623/13.14 |
| 6,099,568 A | * | 8/2000 | Simonian et al. ........ 623/13.11 |
| 6,235,057 B1 | * | 5/2001 | Roger et al. ............. 623/13.12 |
| 6,283,996 B1 | * | 9/2001 | Chervitz et al. ......... 623/13.14 |
| 6,461,373 B2 | * | 10/2002 | Wyman et al. ............. 606/232 |
| 6,562,071 B2 | * | 5/2003 | Jarvinen .................. 623/13.14 |

\* cited by examiner

*Primary Examiner*—David H. Willse
*Assistant Examiner*—Javier G. Blanco
(74) *Attorney, Agent, or Firm*—Workman Nydegger

(57) ABSTRACT

Apparatus is disclosed for reconstructing a ligament, the apparatus including a bone fixation element having a central bore and adapted for positioning in a bone tunnel, a flexible filament configured for holding a graft ligament, and a crimp configured for attachment to the flexible filament so as to prevent movement of the graft ligament in the bone tunnel.

20 Claims, 20 Drawing Sheets

METHOD AND APPARATUS FOR RECONSTRUCTING A LIGAMENT

CROSS-REFERENCE TO RELATED APPLICATIONS

This patent application claims benefit of prior U.S. Provisional Patent Application Ser. No. 60/237,817, filed Oct. 3, 2000 by E. Marlowe Goble for METHOD AND APPARATUS FOR RECONSTRUCTING A LIGAMENT, now abandoned, which patent application is hereby incorporated herein by reference.

BACKGROUND OF THE INVENTION

1. The Field of the Invention

This invention relates to medical procedures and apparatus in general, and more particularly to bone fixation systems and related medical procedures that can be used in reconstructing a ligament.

2. The Relevant Technology

A ligament is a piece of fibrous tissue which connects one bone to another. Ligaments are frequently damaged (e.g., detached or torn or ruptured, etc.) as the result of injury and/or accident. A damaged ligament can impede proper motion of a joint and cause significant pain.

Various procedures have been developed to repair or replace a damaged ligament. The specific procedures used depend on the particular ligament which is to be restored and on the extent of the damage.

One ligament which is frequently damaged as the result of injury and/or accident is the anterior cruciate ligament (ACL). Looking now at FIG. 1, the ACL 5 extends between the top of the tibia 10 and the bottom of the femur 15. A damaged ACL can cause instability of the knee joint and cause substantial pain and arthritis.

Numerous procedures have been developed to restore the ACL through a graft ligament replacement. In general, and looking now at FIG. 2, these ACL replacement procedures involve drilling a bone tunnel 20 through tibia 10 and up into femur 15. Then a graft ligament 25, consisting of a harvested or artificial ligament or tendon(s), is passed through the tibial portion 30 of tunnel 20 (sometimes referred to as the "tibial tunnel"), across the interior of the joint, and up into the femoral portion 35 of tunnel 20 (sometimes referred to as the "femoral tunnel"). Then a distal portion of graft ligament 25 is secured in femoral tunnel 35, and a proximal portion of graft ligament 25 is secured in tibial tunnel 30.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like pars and further wherein.

DETAILED DESCRIPTION OF THE PREFERRED EMBODIMENTS

There are numerous ways in which graft ligament 25 may be loaded into bone tunnel 20 and then secured in position. The present invention is directed to a new method for positioning a graft ligament 25 in bone tunnel 20 and for securing the graft ligament in position, and to new apparatus for use in the same.

Figure 1:
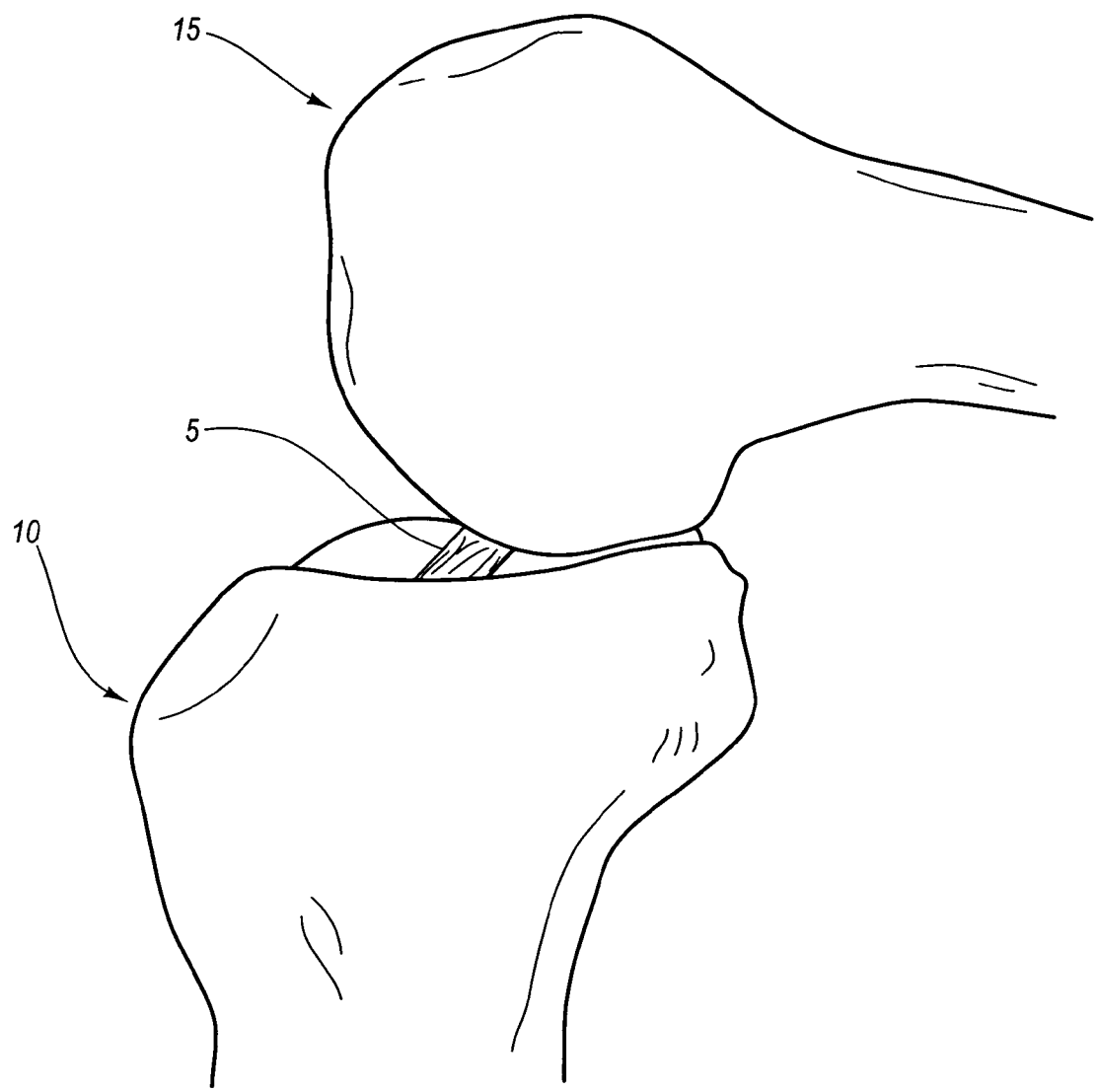
FIG. 1 is an elevated side view of a knee joint having an anterior cruciate ligament.
Figure 2:
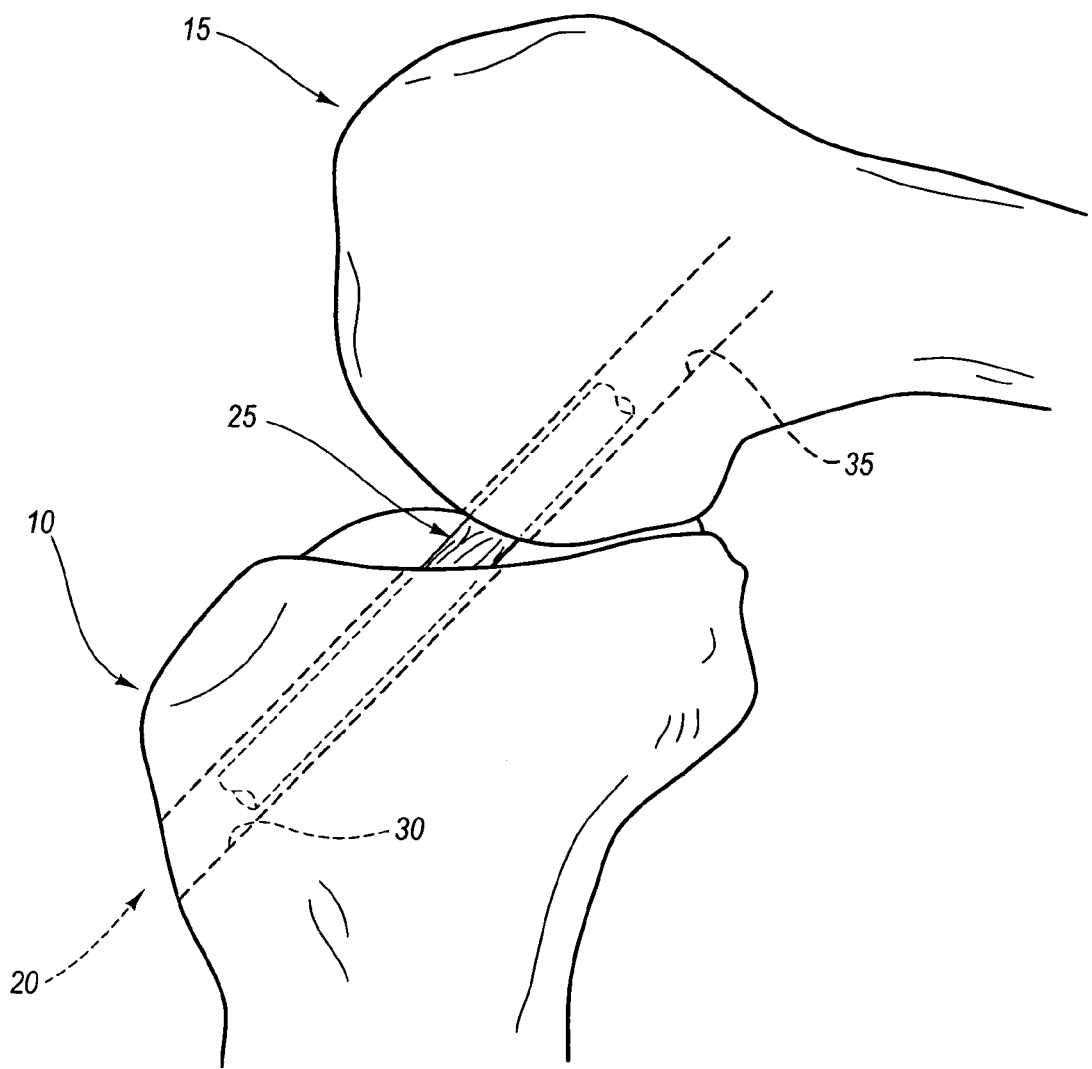
FIG. 2 is a side view of the knee joint shown in FIG. 1 with the anterior cruciate ligament replaced by a graft ligament.
Figure 3:
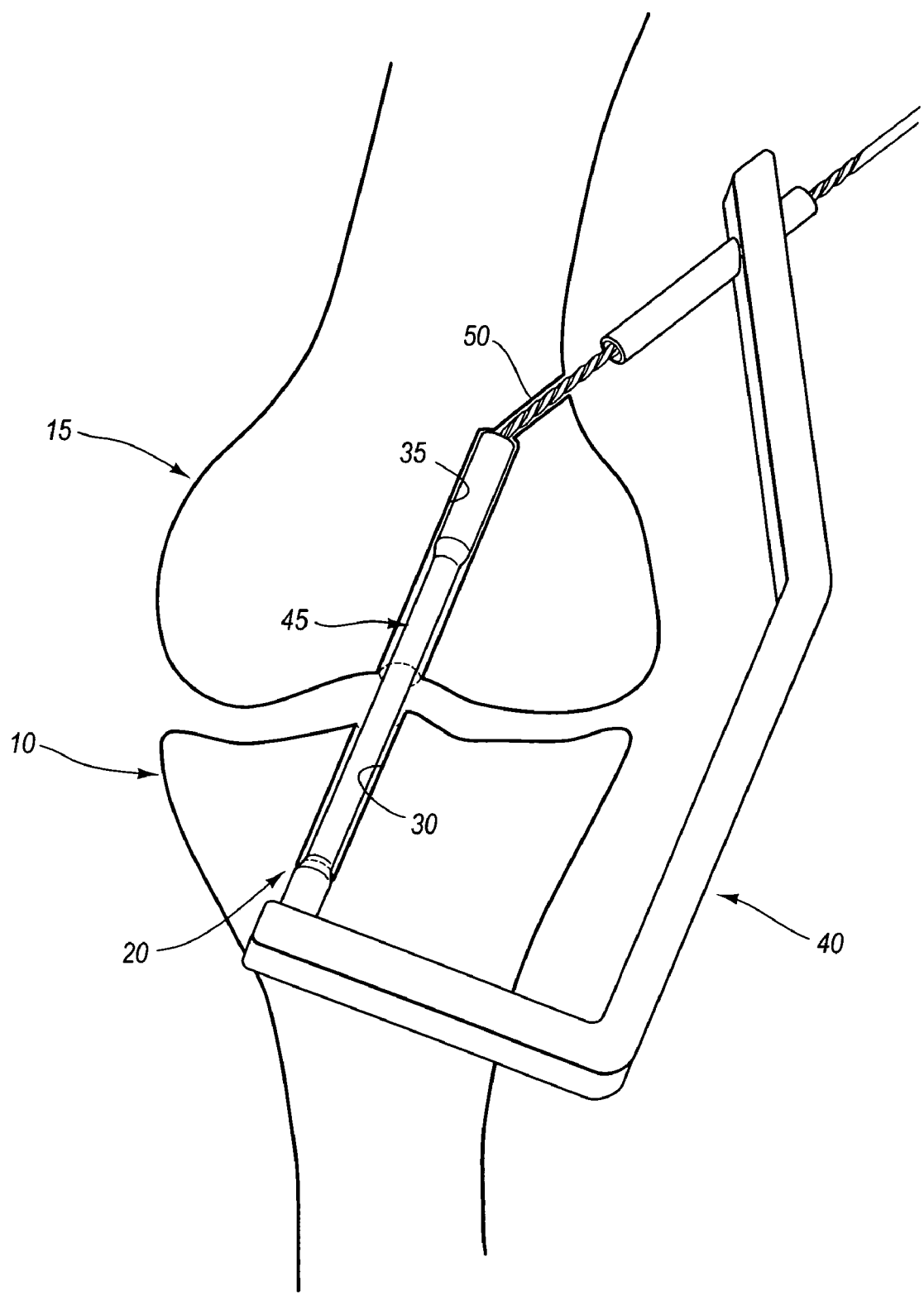
FIG. 3 is a cross sectional side view of a knee joint having a drill guide partially disposed within a bone tunnel formed on the tibia and femur.

More particularly, and looking now at FIG. 3, after bone tunnel 20 (consisting of tibial tunnel 30 and femoral tunnel 35) has been drilled, a drill guide 40 is inserted into the bone tunnel 20. Specifically, the drill guide 40 has an endosteal guide 45 passed up tibial tunnel 30, across the interior of the knee joint, and then up femoral tunnel 35. Then an anterolateral portal is made on the anterior border of the IT band, and an angled tunnel 50 is drilled from the periosteum to the proximal end of femoral tunnel 35. Thus, angled tunnel 50 opens on, and communicates with, femoral tunnel 35. In this respect it should be appreciated that drill guide 40 is essentially a cross-pin drill guide of the sort well known in the art, except modified so as to enable the angled tunnel 50 to be drilled at an acute angle (e.g., 45 degrees) to the axis of femoral tunnel 35.

Figure 4:
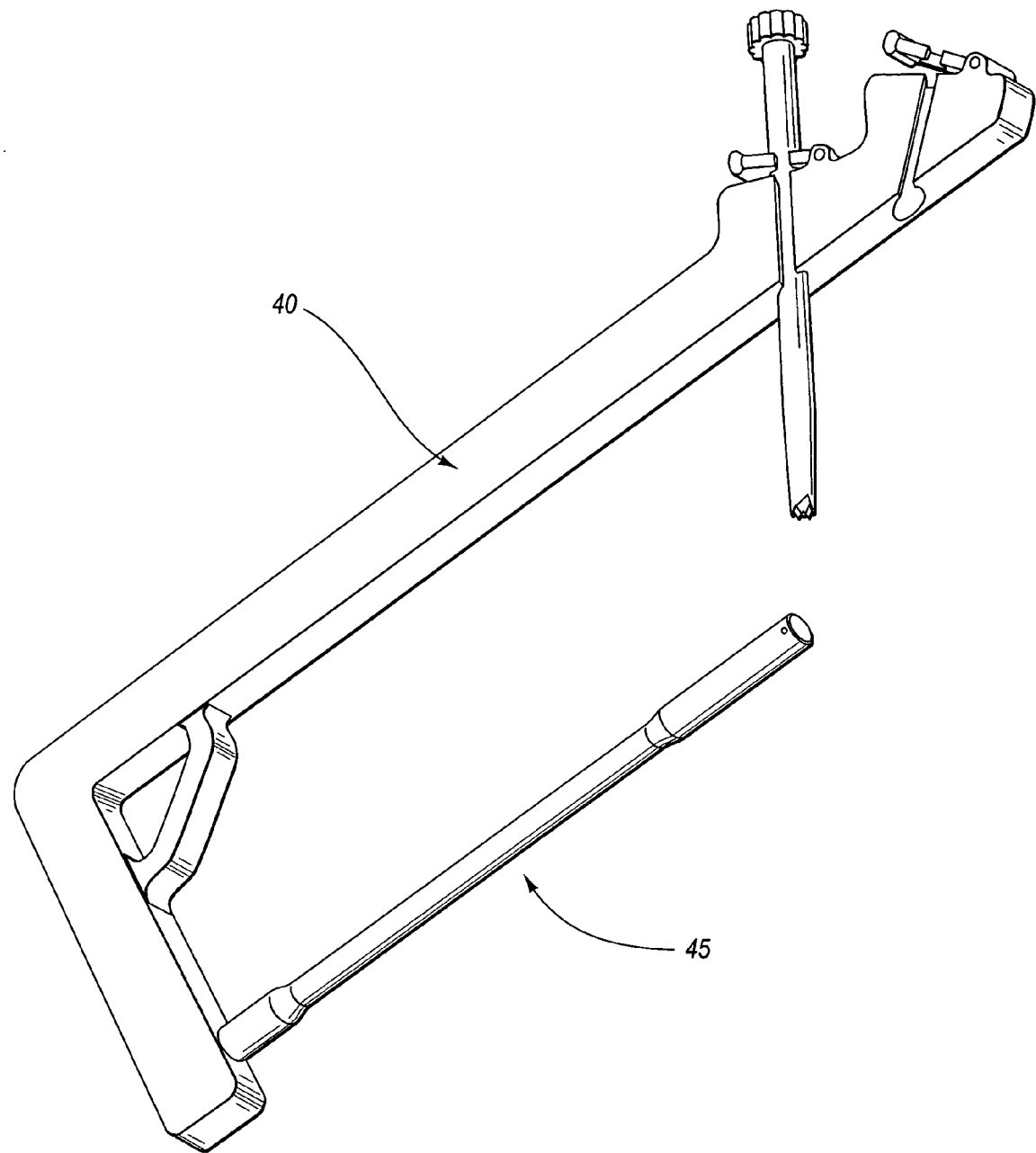
FIG. 4 is a perspective view of an alternative embodiment of the drill guide shown in FIG. 3.
Figure 5:
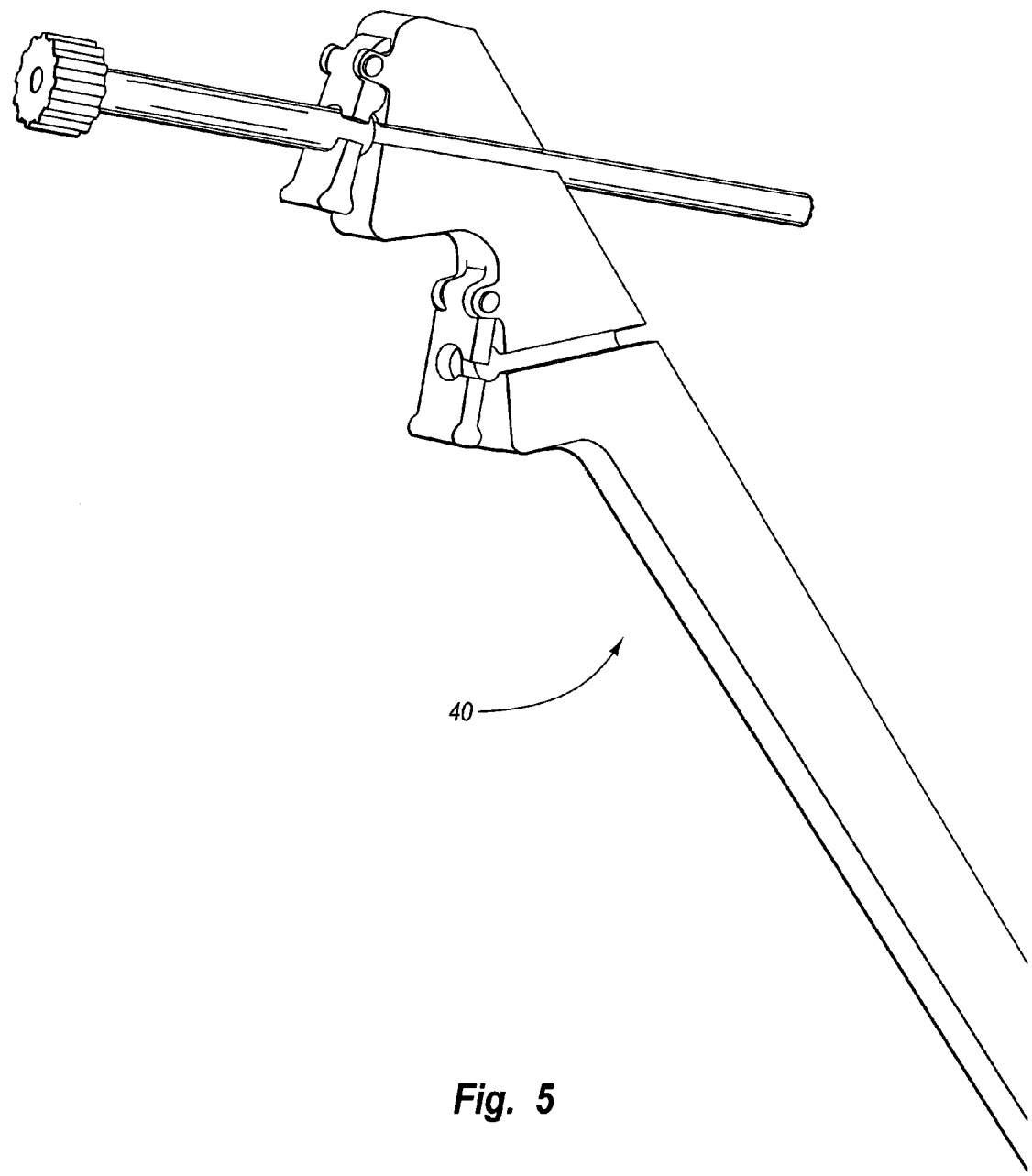
FIG. 5 is a top perspective view of a portion of the drill guide shown in FIG. 4.
Figure 6:
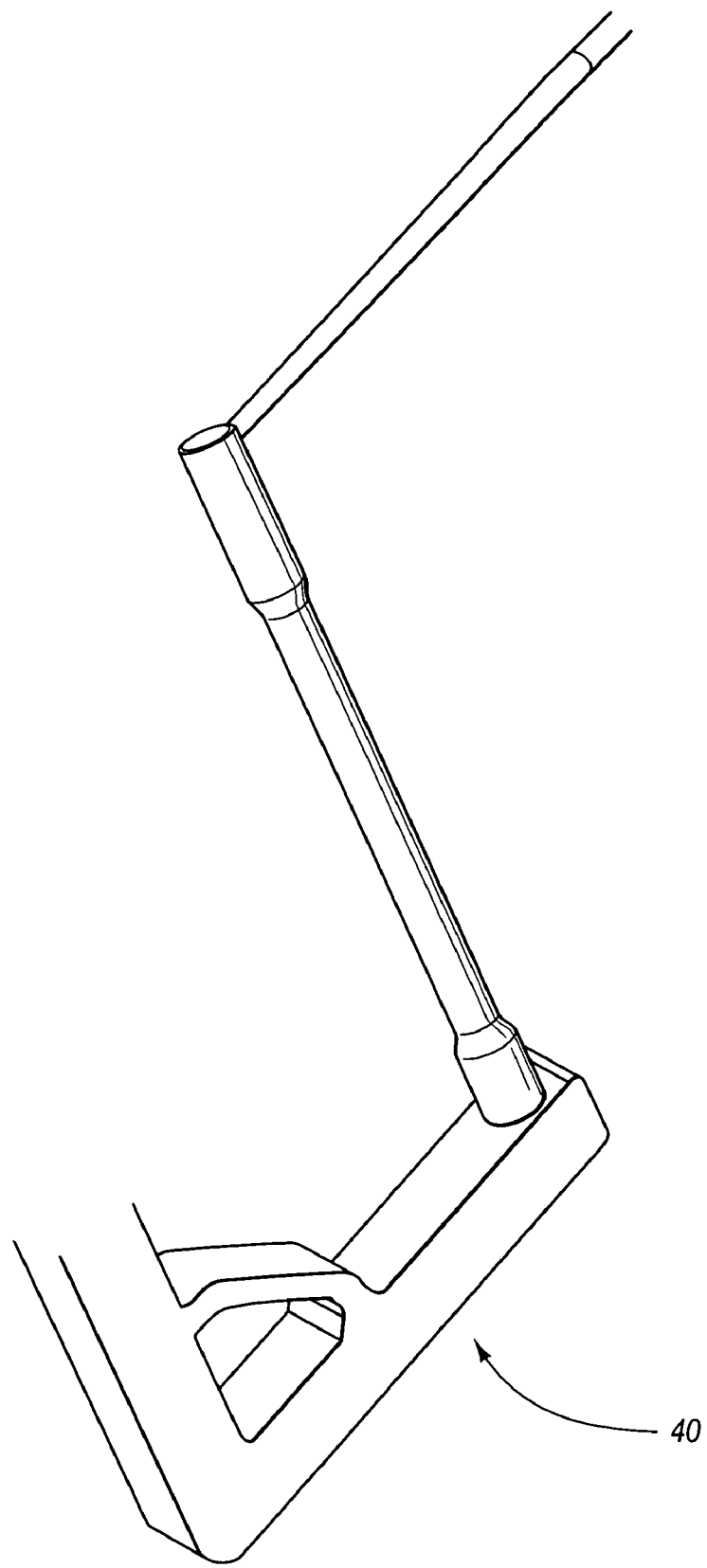
FIG. 6 is a bottom perspective view of a portion of the drill guide shown in FIG. 4.

If desired, drill guide 40 can be set so as to always drill the angled tunnel 50 at the same angle (e.g., 30 or 45 or 60 degrees, etc.), or the approach may be straight, i.e., aligned with the femoral tunnel (e.g., at 0 degrees), or drill guide 40 can be configured so as to be adjustable, whereby the surgeon can select the specific angle of angled tunnel 50. By way of example but not limitation, some details regarding the construction of one preferred form of drill guide 40 is shown in FIGS. 4–6.

Figure 7:
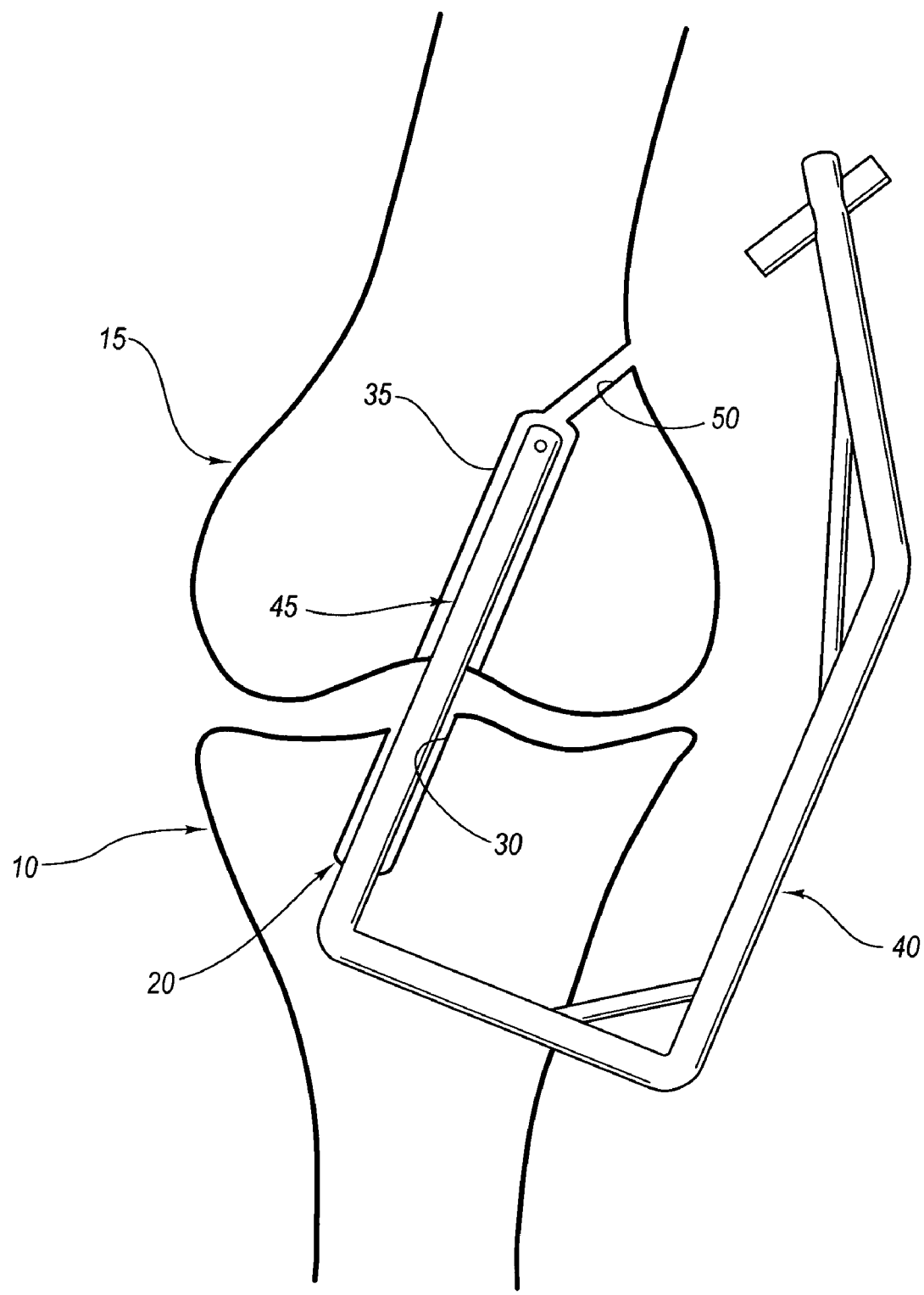
FIG. 7 is a cross sectional side view of the knee joint shown in FIG. 3 having the drill and barrel guide removed.

Looking next at FIG. 7, after angled tunnel 50 is drilled, the drill and barrel guide are removed from drill guide 40. The drill guide 40 is then rotated about the axis of bone tunnel 20 so as to swing the head of drill guide 40 away from the entrance to angled tunnel 50, whereby to provide convenient access to the entrance of angled tunnel 50.

Figure 8:
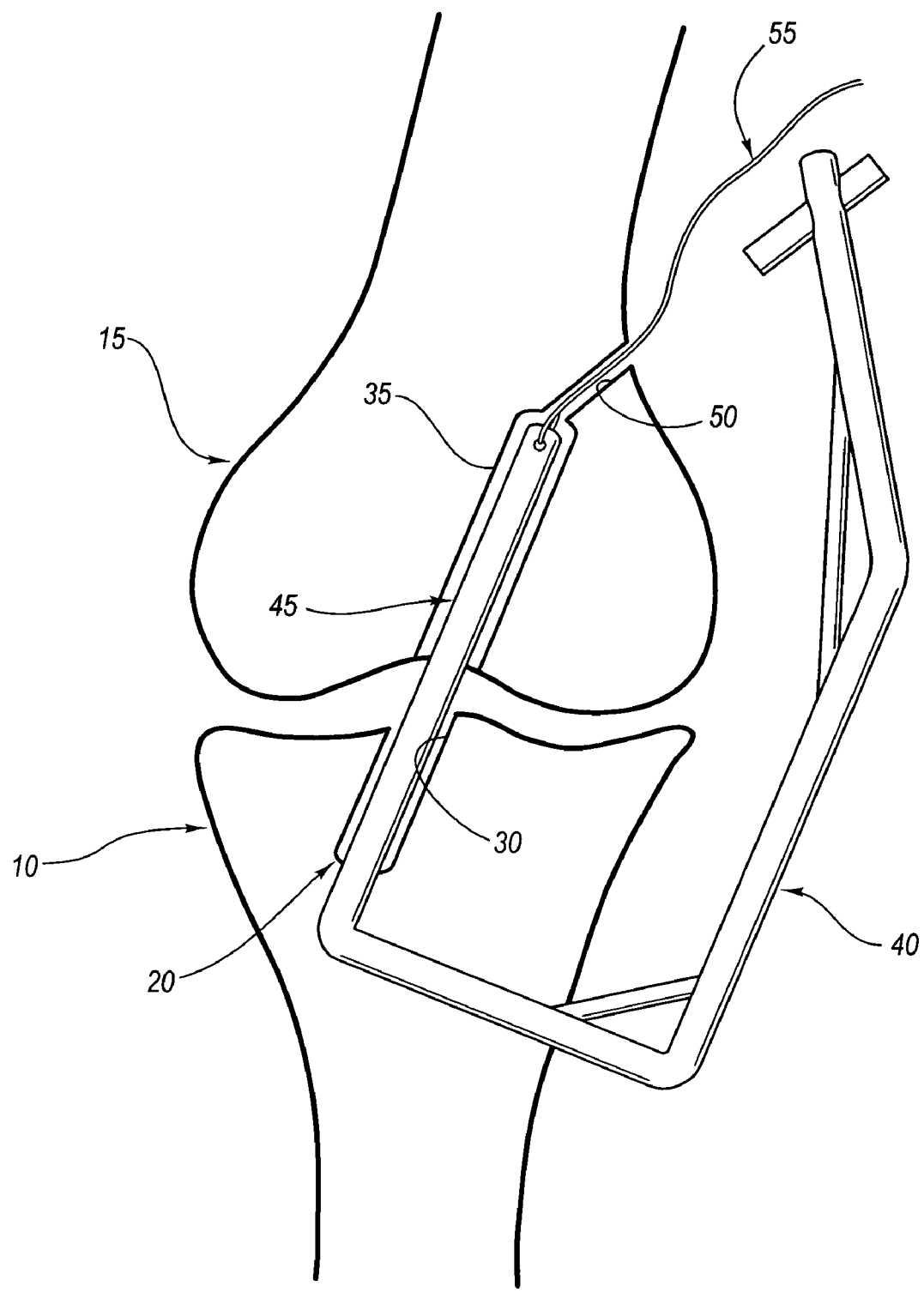
FIG. 8 is a cross sectional side view of the knee joint shown in FIG. 7 with a suture engaged with the endosteal guide.

Looking next at FIG. 8, a braided wire suture 55 is inserted down angled tunnel 50 and "grabbed" by the distal end of endosteal guide 45. To this end, the endosteal guide 45 may include some sort of grippers at its distal end, or the end of the wire suture 55 may include a loop at its distal end and the endosteal guide 45 may include some sort of hook at its distal end, or the end of the endosteal guide 45 may include some sort of loop at its distal end and the end of the wire suture 55 may include some sort of hook at its distal end, etc. Alternatively, endosteal guide 45 may be cannulated so as to permit grippers or a hook to be passed down the interior of the endosteal guide 45 to grab the distal end of the wire suture 55. In any case, the endosteal guide 45 and wire suture 55 are configured so as to permit the distal end of the endosteal guide 45 to connect up with the distal end of the wire suture 55.

Figure 9:
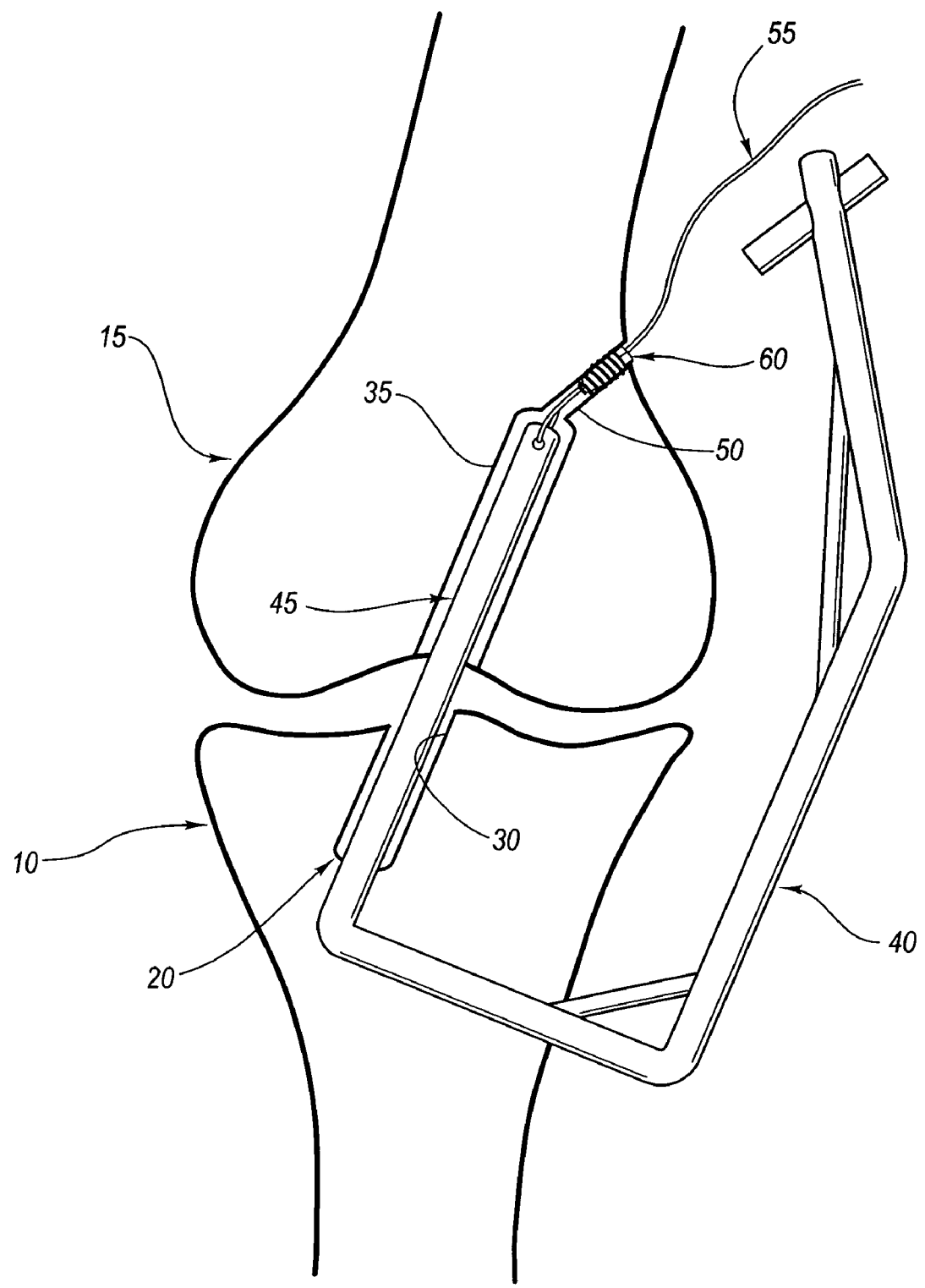
FIG. 9 is a cross sectional side view of the knee joint shown in FIG. 8 with a cannulated screw passed over the suture and driven into the angled tunnel.

Referring next to FIG. 9, once the distal end of endosteal guide 45 is connected with the distal end of wire suture 55, a cannulated screw 60 is slid down the wire suture 55 and screwed into angled tunnel 50. This can be done by using a cannulated driver (not shown in FIG. 9) of the sort well known in the art. Cannulated screw 60 is screwed into femur 10 until the head of the screw 60 contacts the periosteum so that the head of the screw 60 does not stand proud above the bone. Cannulated screw 60 essentially acts as a sort of liner for angled tunnel 50, providing a bearing surface for wire suture 55 so as to prevent the wire suture 55 from cutting into femur 15 as the wire suture 55 is moved through angled tunnel 50, as will hereinafter be discussed.

Figure 10:
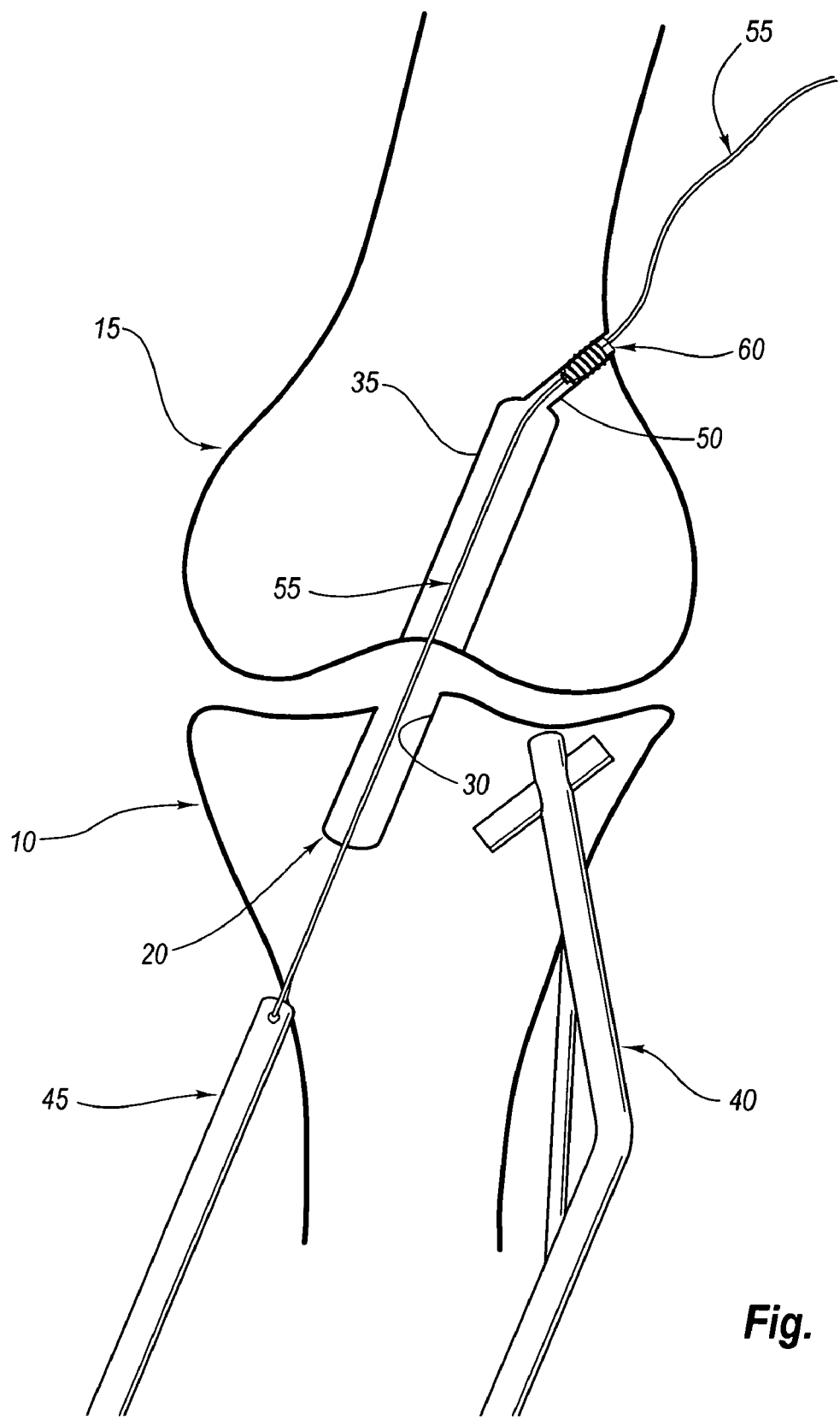
FIG. 10 is a cross sectional side view of the knee joint shown in FIG. 9 with the endosteal guide removed from the bone tunnel.

Next, and looking now at FIG. 10, drill guide 40 is withdrawn from the surgical site. As this occurs, the endosteal guide 45 of drill guide 40 is removed from bone tunnel 20, causing wire suture 55 to be pulled down femoral tunnel 35, across the interior of the knee joint, down tibial tunnel 30 and then out the bottom end of the tibial tunnel 30.

Figure 11:
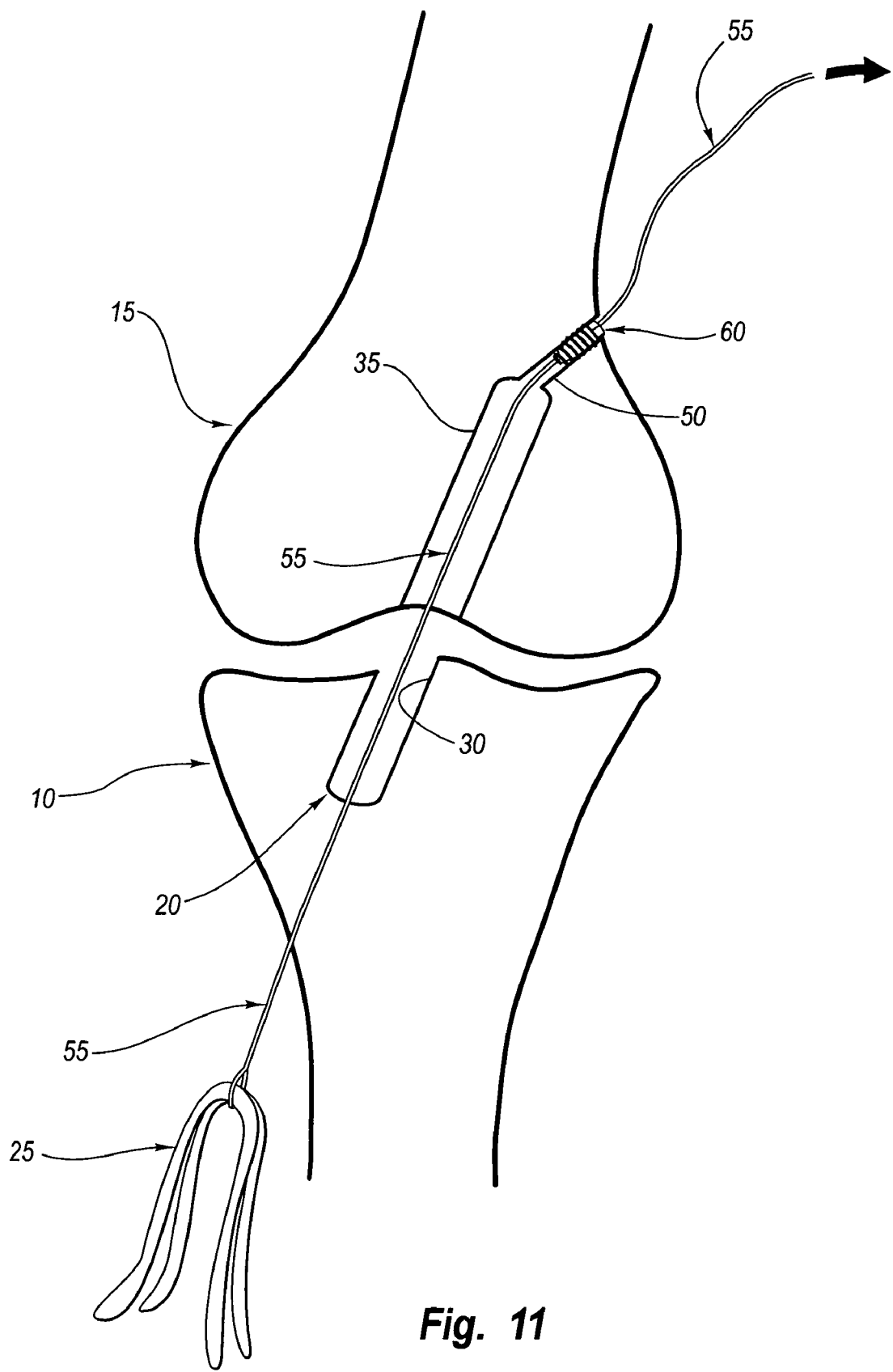
FIG. 11 is a cross sectional side view of the knee joint shown in FIG. 10 with a graft ligament attached to the suture.

Then, as shown in FIG. 11, the graft ligament 25, e.g., one or more strands of a hamstring tendon, is attached to the distal end of wire suture 55. In the case where the graft ligament 25 comprises one or more strands of hamstring tendon, such attachment can be easily accomplished by forming a loop at the lower end of wire suture 55 and then passing the tendon strand(s) through the loop, in the manner shown in FIG. 11.

Figure 12:
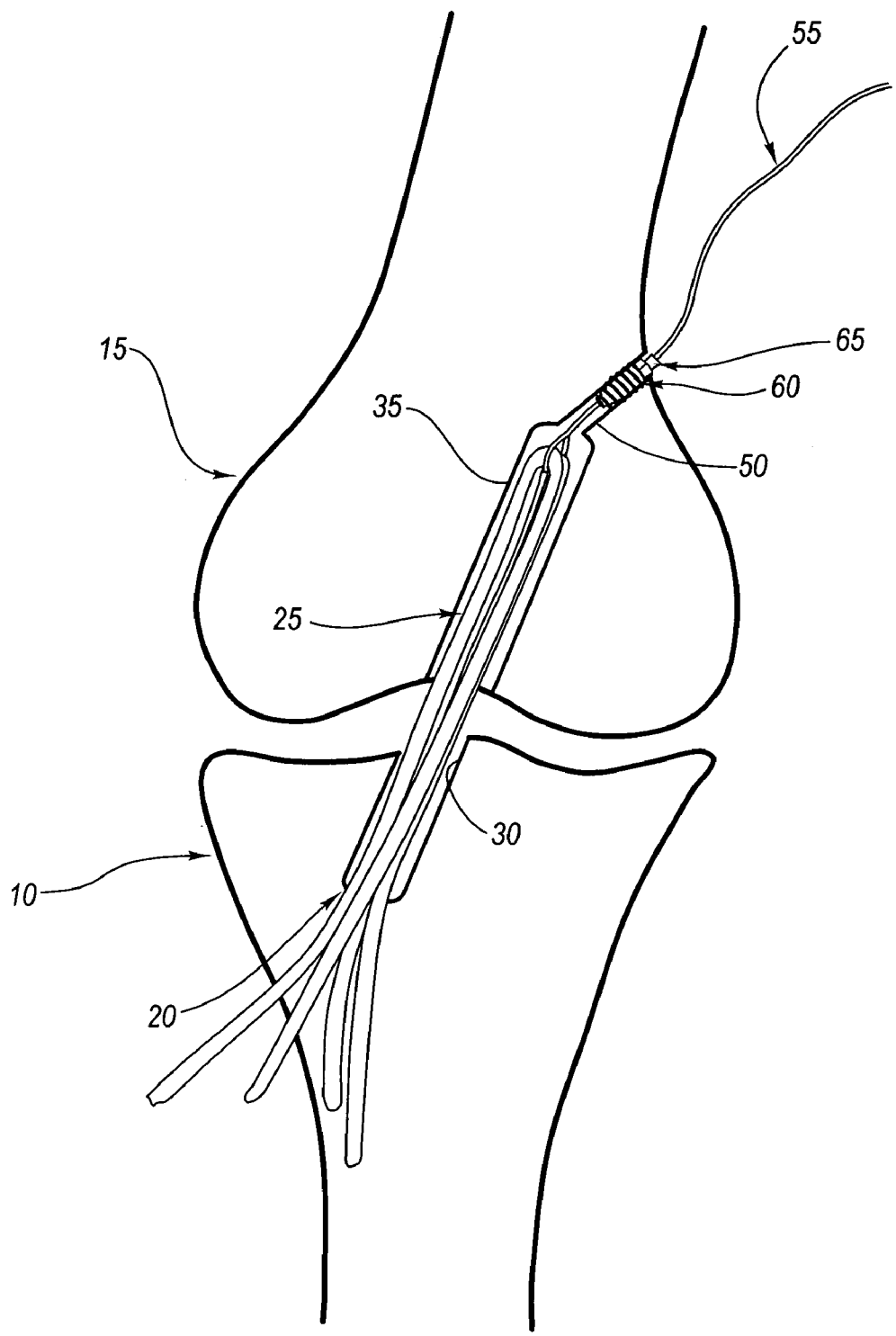
FIG. 12 is a cross sectional side view of the knee joint shown in FIG. 11 with the draft ligament drawn into the bone tunnel and a crimp secured to the suture.

Next, as shown in FIG. 12, wire suture 55 is pulled proximally so as to tow graft ligament 25 up bone tunnel 20 until the distal end of the graft ligament 25 is positioned in femoral tunnel 35 and the proximal end of the graft ligament 25 is positioned in tibial tunnel 30. Then a crimp 65 is attached to wire suture 55 adjacent to cannulated screw 60 so that engagement of crimp 65 with cannulated screw 60 will prevent the wire suture 55 from being pulled back in the tibial direction. Next, graft ligament 25 is tensioned by pulling the proximal end of the graft ligament 25 in the proximal direction. The proximal end of the graft ligament 25 is then fixed to the tibia in ways well known in the art.

If desired, the proximal end of cannulated screw 60 can have a modest recess therein so as to receive crimp 65 when the ligament is tensioned, whereby to keep the crimp from standing proud above the femur. Alternatively, the bone screw 60 can be eliminated, utilizing only the crimp 65 on the wire suture 55 to prevent distal migration. Finally, the end of wire suture 55 proximal to crimp 65 is trimmed off, thus effectively completing the ACL reconstruction procedure.

In the foregoing description, and in FIGS. 11 and 12, graft ligament 25 was discussed in the context of comprising one or more strands of hamstring tendon. However, it should also be appreciated that graft ligament 25 may comprise other constructs as well. Thus, for example, graft ligament 25 may comprise one or more bone blocks attached to a tendon (e.g., a so-called "bone-tendon-bone" graft), or a totally artificial prosthesis, etc.

Figure 13:
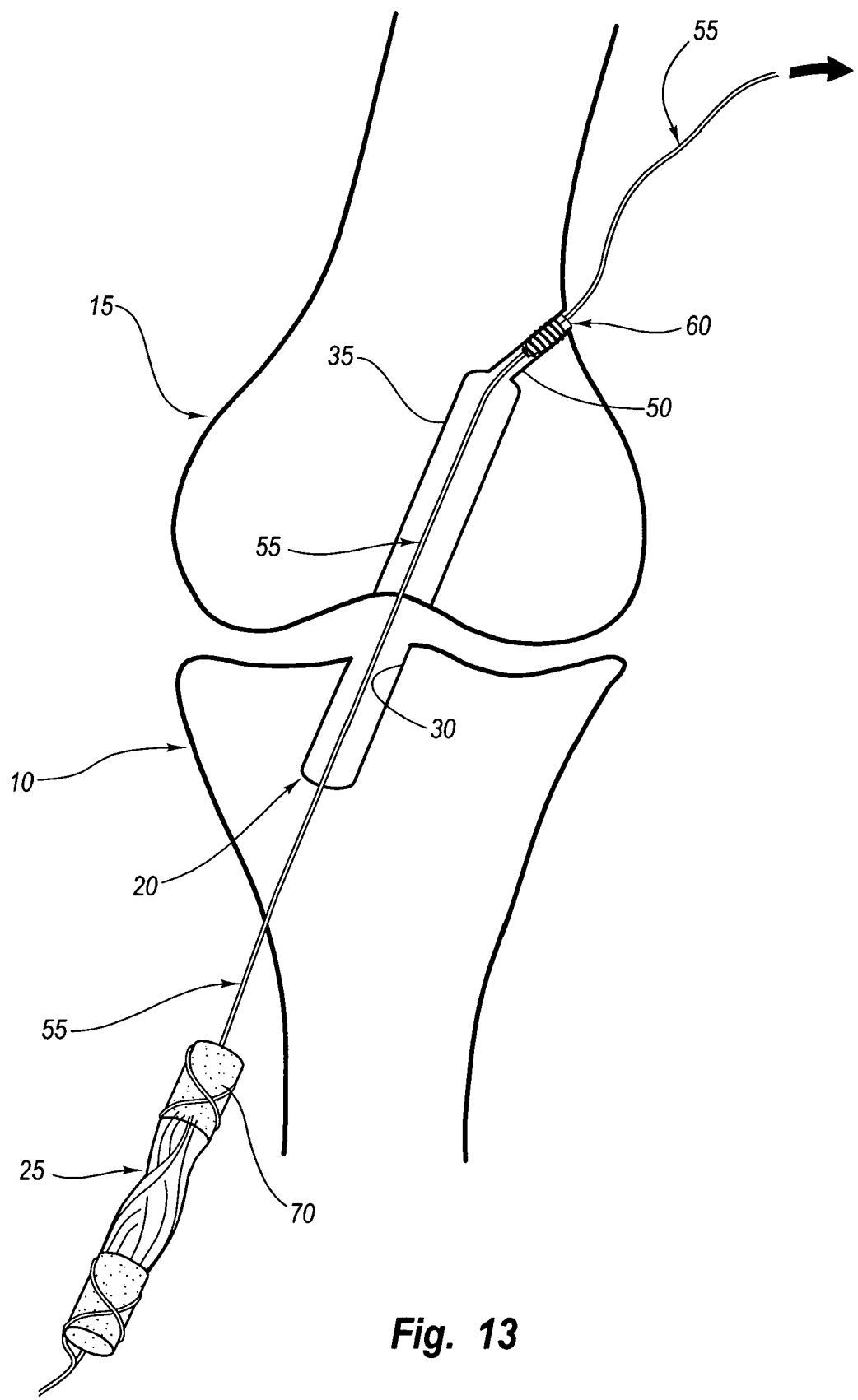
FIG. 13 is a cross sectional side view of the knee joint shown in FIG. 12 wherein the graft ligament is depicted as a bone-tendon-bone graft that is coupled with the suture and is disposed outside of the bone tunnel.
Figure 14:
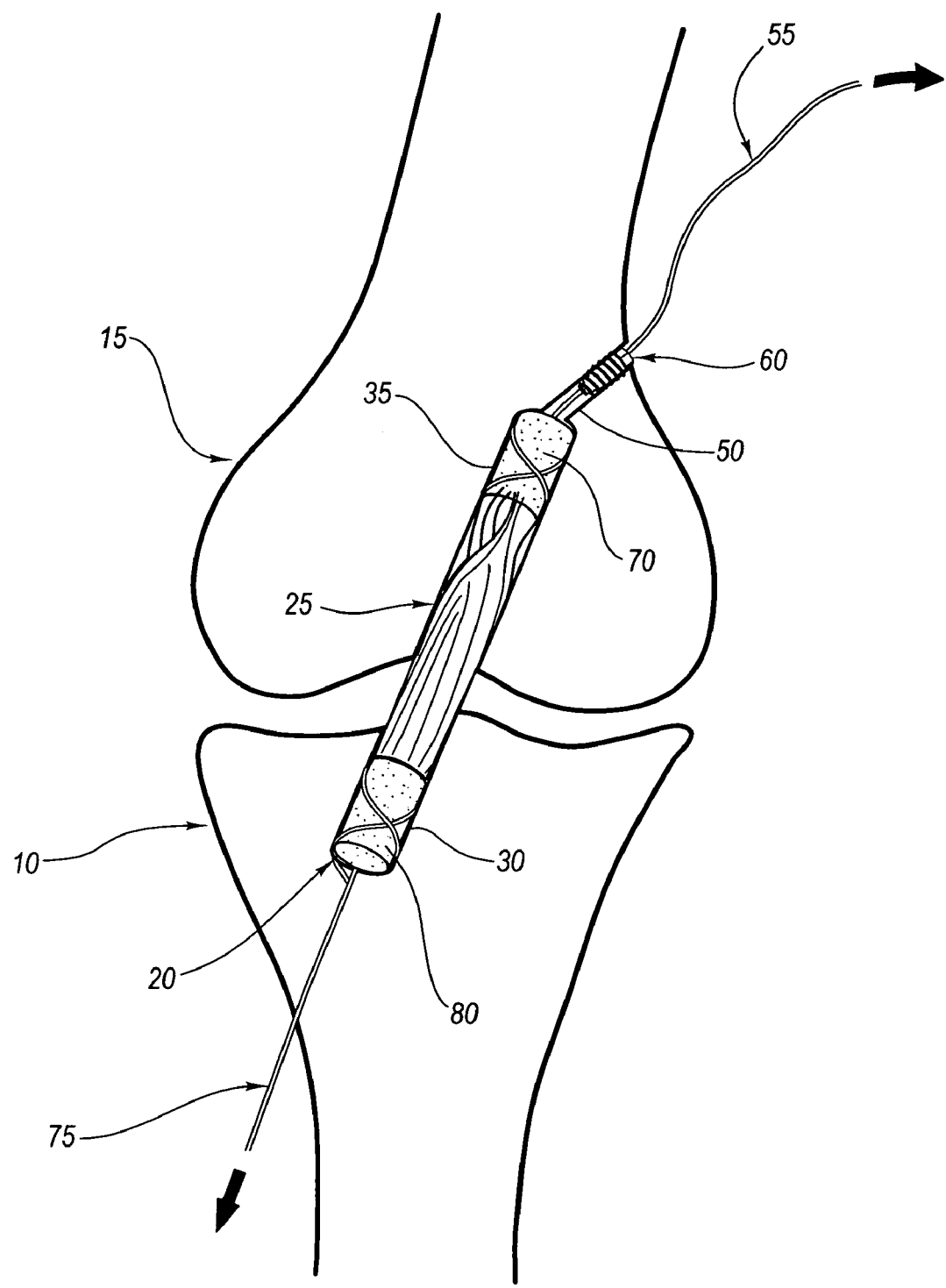
FIG. 14 is a cross sectional side view of the knee joint shown in FIG. 13 wherein the bone-tendon-bone graft is drawn into the bone tunnel.

By way of example but not limitation, FIGS. 13 and 14 show a bone-tendon-bone graft being towed into position within bone tunnel 20. In this case, wire suture 55 may be attached to the leading bone block 70, e.g., by passing the wire suture 55 through one or more holes formed in the bone block 70 and making it fast. If desired, a second wire suture 75 may be attached to the trailing bone block 80 so as to fasten the trailing end of the ligament graft to tibia 10 in ways well known in the art.

Figure 15:
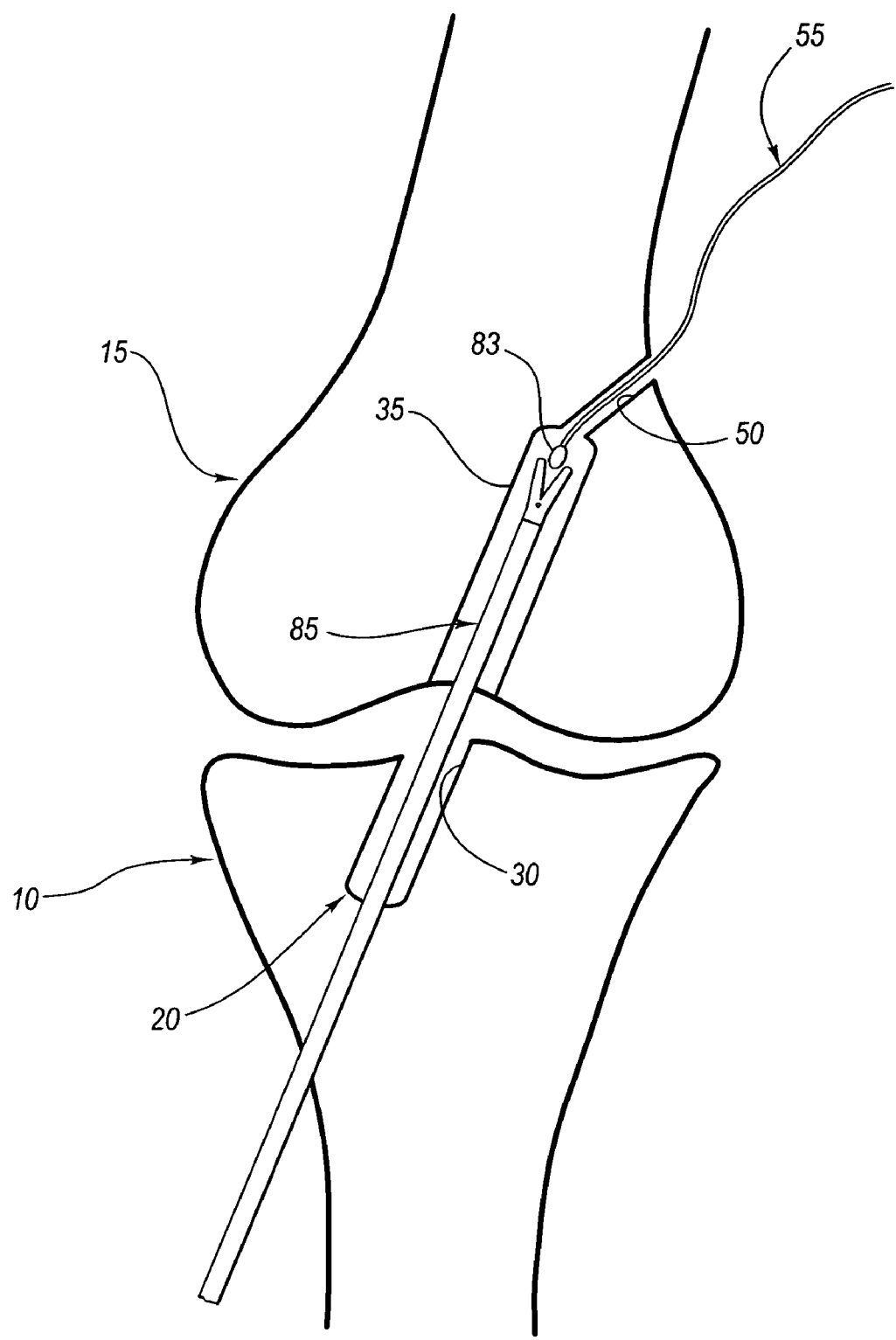
FIG. 15 is a cross sectional side view of the knee joint shown in FIG. 7 wherein a grasper disposed within the bone tunnel is grasping a suture passed through the angled tunnel.

It should be appreciated that the aforementioned procedure and apparatus may be modified without departing from the scope of the present invention. Thus, for example, and looking now at FIG. 15, in one alternative reconstruction procedure, after angled tunnel 50 has been drilled, drill guide 40 is completely removed from the surgical site. Then a wire suture 55, preferably having a loop 83 at its distal end, is passed down angled tunnel 50 until the wire suture 55 begins to pass into the top end of femoral tunnel 35.

Figure 16:
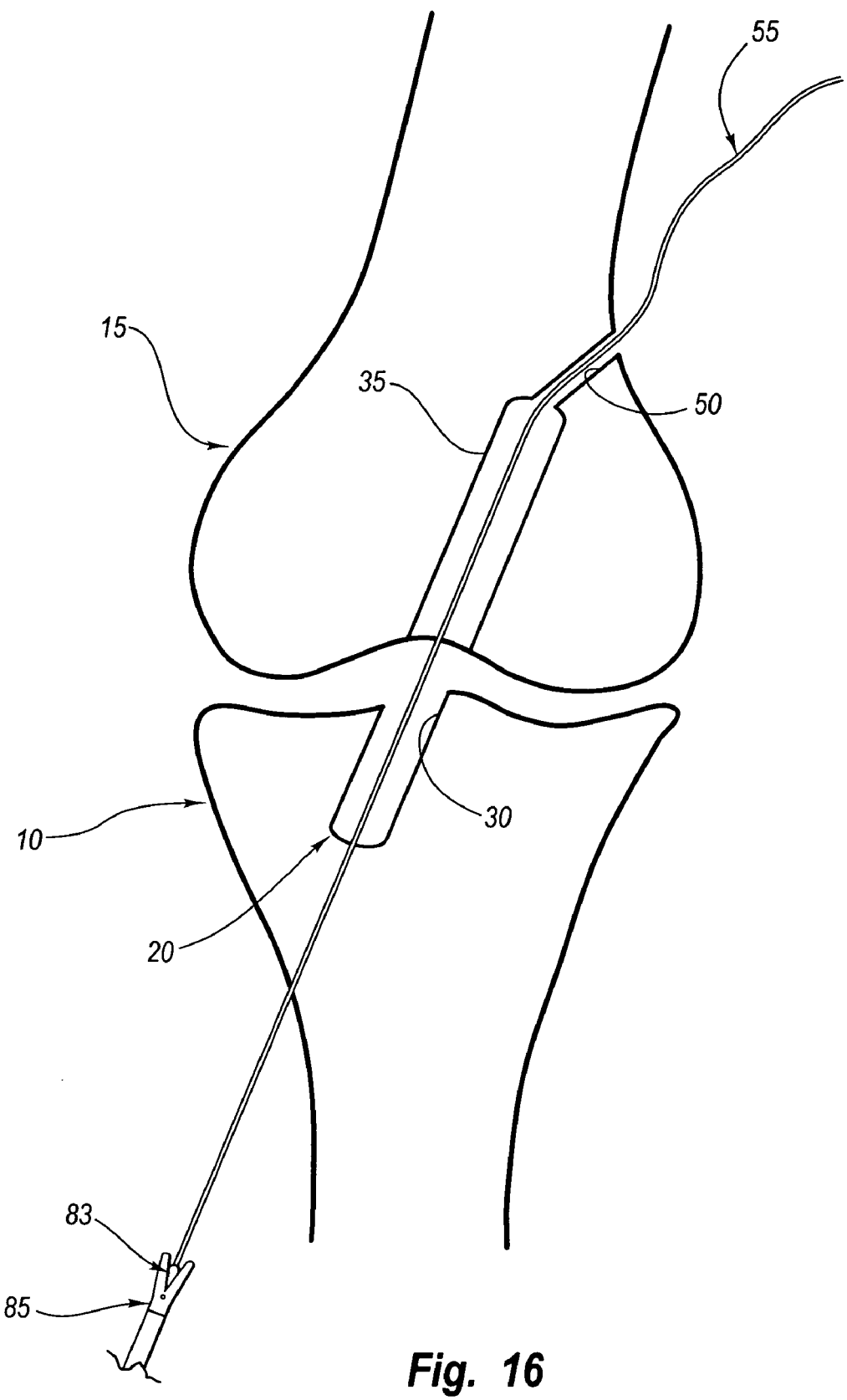
FIG. 16 is a cross sectional side view of the knee joint shown in FIG. 7 wherein the suture has been pulled through the bone tunnel by the grasper.

Next, a suture grasper 85 passed up bone tunnel 20 until the distal end of the suture grasper 85 is positioned adjacent to the distal end of wire suture 55. The suture grasper 85 is then used to pick up the distal end of wire suture 55 and draw the wire suture 55 down femoral tunnel 35, across the interior of the knee joint, down tibial tunnel 30, and finally out the front of tibia 10, as shown in FIG. 16. The cannulated screw 60 can then be mounted on the proximal end of wire suture 55, the cannulated screw 60 screwed down into the periosteum, the distal end of wire suture 55 fastened to the graft ligament 25, the wire suture 55 retracted so as to tow the graft ligament 25 up bone tunnel 20 and into position, the crimp 65 applied to the wire suture 55, and then the graft ligament 25 made fast to the tibia, all in substantially the same manner as previously described.

Figure 18:
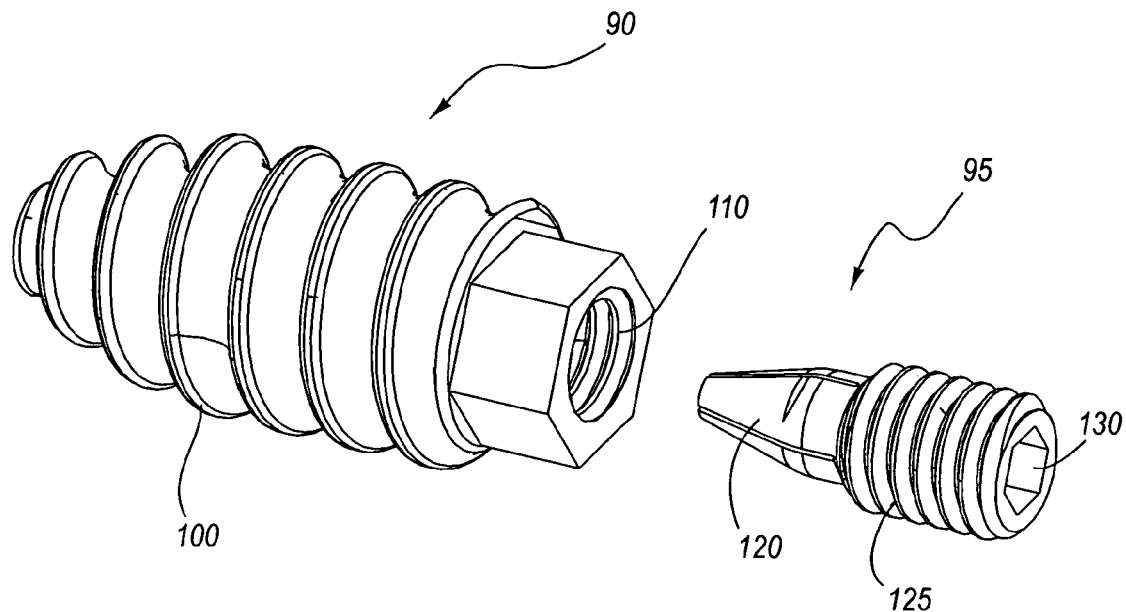
FIG. 18 is a back perspective view of the cannulated screw and collet shown in FIG. 17.
Figure 19:
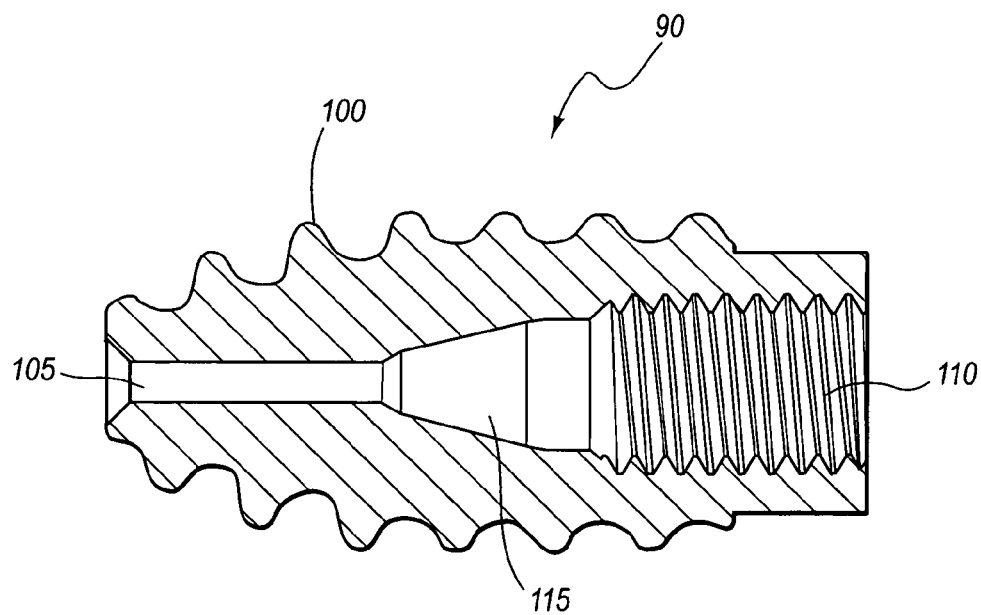
FIG. 19 is a cross sectional side view of the cannulated screw shown in FIG. 18.
Figure 20:
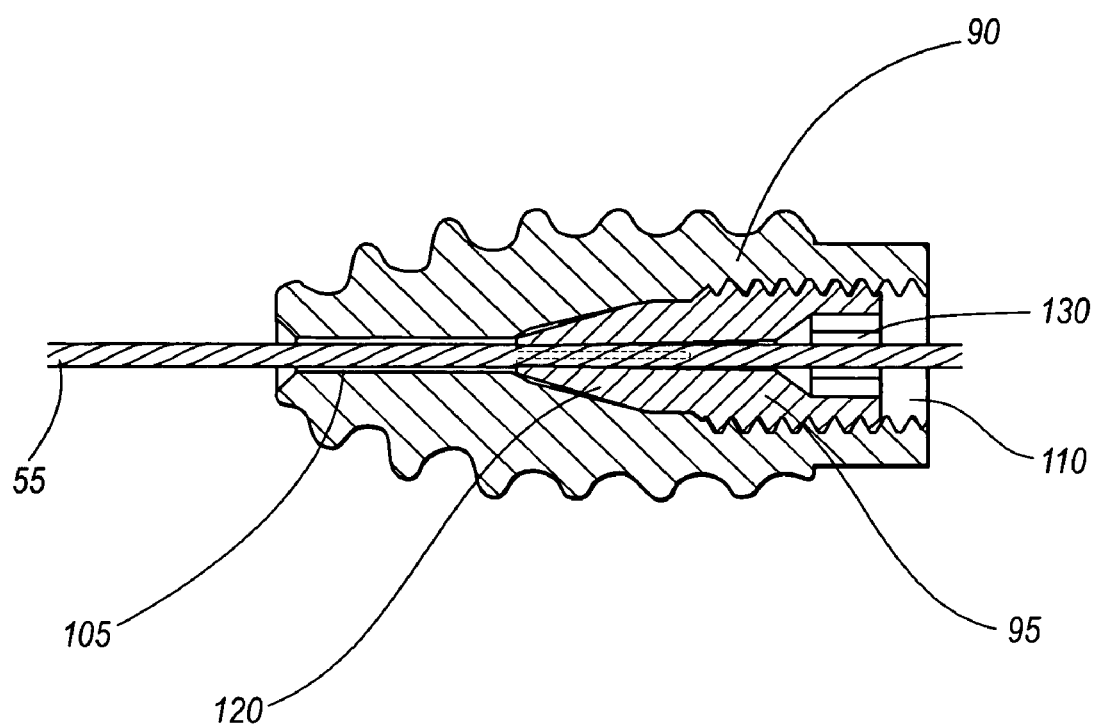
FIG. 20 is a cross sectional side view of the assembled suture, cannulated screw, collet shown in FIG. 17.

In another alternative reconstruction procedure, cannulated screw 60 and crimp 65 may be replaced by an alternative construction. More particularly, and looking now at FIGS. 17–19, a cannulated screw 90 and an associated threaded collet 95 are shown. Cannulated screw 90 has the usual external threads 100 and central bore 105. Cannulated screw 90, however, also has a threaded counterbore 110 terminating, intermediate the cannulated screw 90, in a smooth tapered section 115. Correspondingly, threaded collet 95 comprises a leading tapered section 120, a trailing threaded section 125, and a central bore 130. The leading tapered section 120 of collet 95 is slit, whereby the tapered section 120 can be forced radially inward so as to close down the diameter of the central bore 130 of collet 95. Depicted in FIG. 20, cannulated screw 90 and threaded collet 95 are sized so that the threaded collet 95 may be lightly screwed into the rear of cannulated screw 90 and wire suture 55 threaded therethrough. Thereafter, threaded collet 95 may be screwed further into cannulated screw 90 so that the nose of the threaded collet 95 will close down on wire suture 55, thereby clamping the wire suture 55 to the threaded collet 95 and, hence, to the cannulated screw 90.

Figure 17:
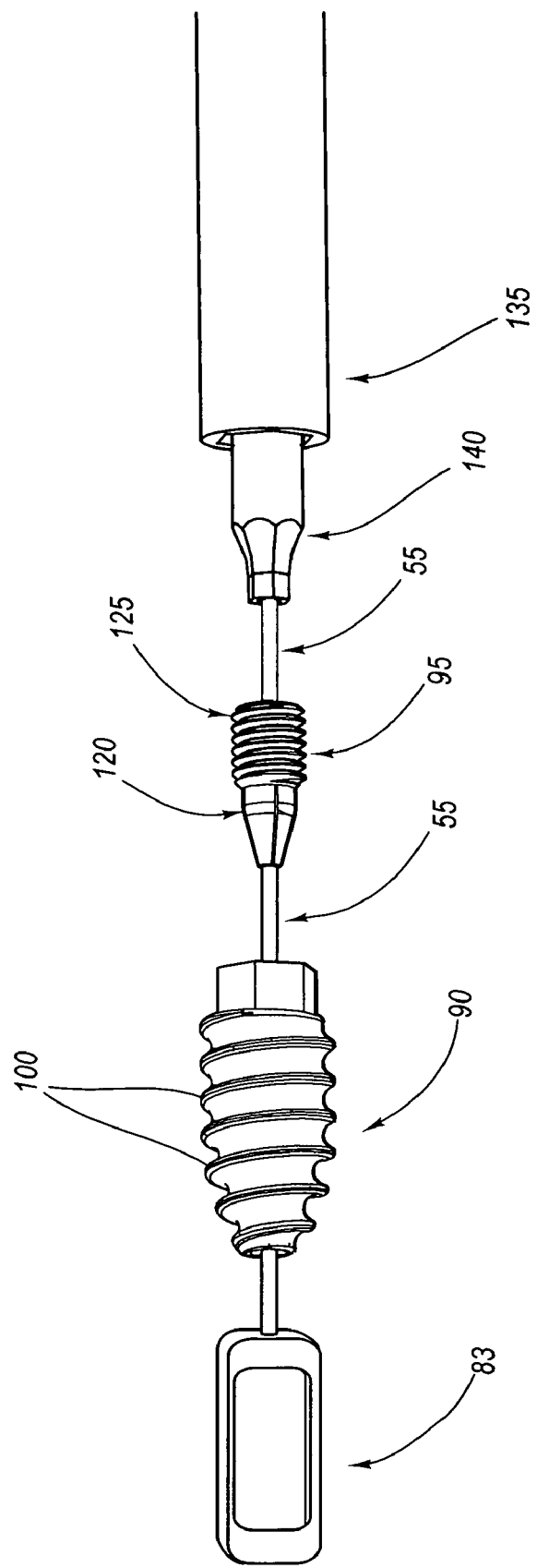
FIG. 17 is an elevated side view of an assembly including a suture, cannulated screw, collet, and drivers.
Figure 21:
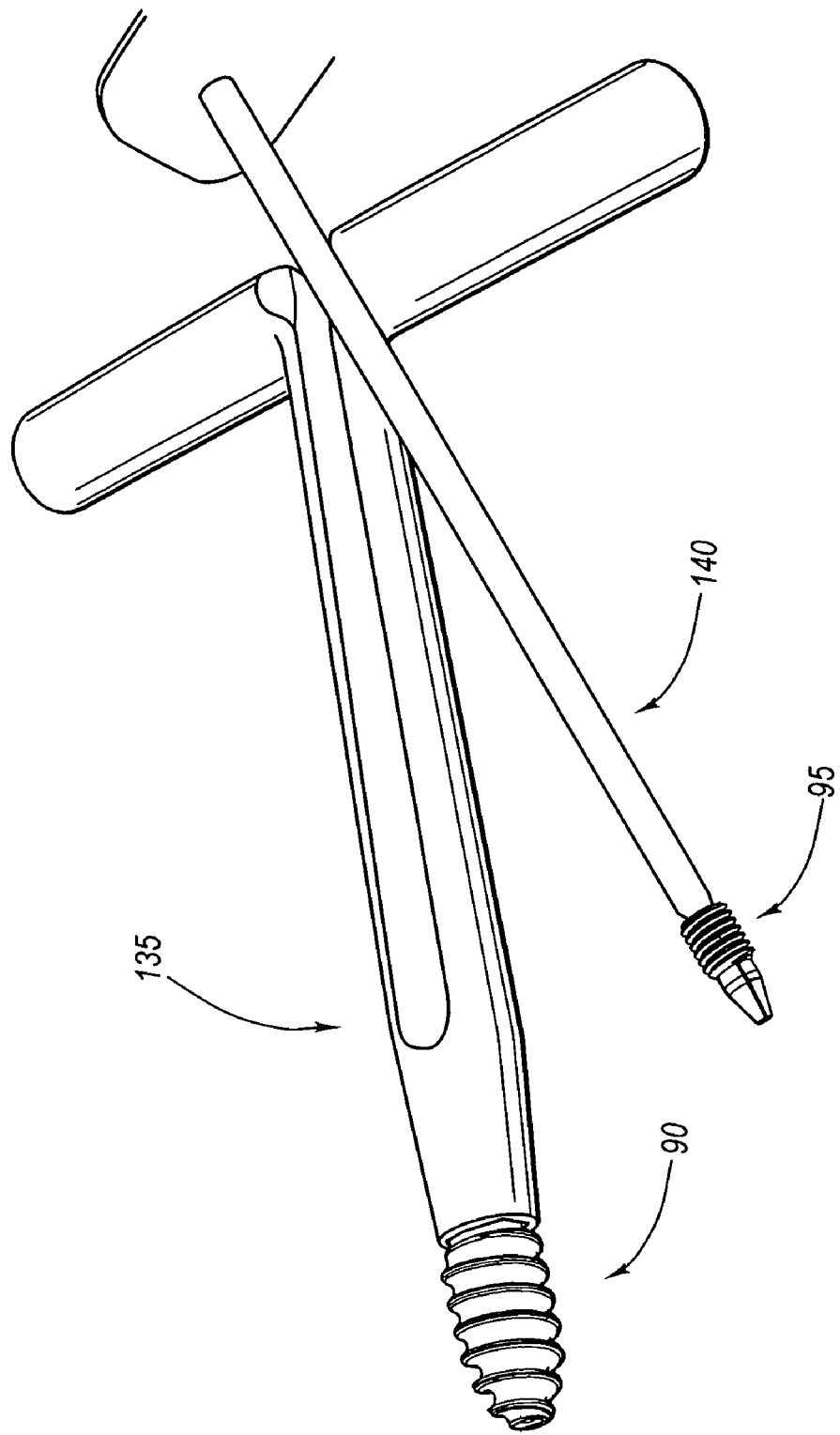
FIG. 21 is a perspective view of the driver for driving the cannulated screw and the driver for driving the collet as shown in FIG. 17.

FIGS. 17 and 21 show drivers for advancing and, alternatively, retracting cannulated screw 90 and threaded collet 95. More particularly, a first cannulated driver 135 is provided for turning cannulated screw 90. A second cannulated driver 140 is provided for turning threaded collet 95. Second cannulated driver 140 may be positioned within first cannulated driver 135, as will hereinafter be discussed.

In use, after wire suture 55 had been passed through angled tunnel 50, cannulated screw 90, threaded collet 95, second driver 140 and first driver 135 are mounted on the proximal end of wire suture 55 (FIG. 17). Next, the components are manipulated so that threaded collet 95 is lightly threaded into cannulated screw 90, second driver 140 is engaged with threaded collet 95, and first driver 135 is engaged with cannulated screw 90. Then the aforementioned assembly is moved down wire suture 55 until the leading tip of cannulated screw 90 engages the femur, whereupon first driver 135 is used to drive the cannulated screw into the femur.

At this point, cannulated screw 90 lines angled tunnel 50, but wire suture 55 is free to move relative to cannulated screw 90 and, hence, the patient's anatomy. Wire suture 55 is then used in the manner previously described to pick up graft ligament 25 and tow the graft ligament 25 back up into position within the bone tunnel. Once the graft ligament 25 is in position, wire suture 55 is made fast by screwing threaded collet 95 further into cannulated screw 90, using second driver 140, until the leading tip of the threaded collet 95 closes down on wire suture 55, whereupon the wire suture 55 is clamped to the threaded collet 95 and, hence, the cannulated screw 90. Once this has been achieved, drivers 135 and 140 may be removed, the excess wire 55 trimmed away, and the tibial side of the graft secured.

It should also be appreciated that the procedure and apparatus described above may be used for purposes other than an ACL repair, e.g., they may be used to repair other ligaments, the apparatus may be used in other types of surgical procedures such as trauma, spine, etc.

Also, the wire suture may be braided polyethylene or monofilament suture; and the cannulated screw and/or threaded collet may be plastic or even reabsorbable.

What is claimed is:

1. Apparatus for reconstructing a ligament, said apparatus comprising:
    a bone fixation element having a distal end, a proximal end, and a central bore extending between said distal end and said proximal end, said central bore having a first diameter, said bone fixation element having an exterior surface with a thread outwardly projecting therefrom and said bone fixation element being adapted for positioning in a bone tunnel;
    a flexible filament having a distal end and a proximal end, said distal end having retaining means for holding a graft ligament, and said flexible filament having a second diameter smaller than said first diameter so as to allow said flexible filament to slidingly pass through said central bore of said bone fixation element, whereby said flexible filament holding the graft ligament in the bone tunnel is slideably positionable through said central bore of said bone fixation element; and
    a crimp crimped onto said flexible filament such that said crimp is securely fixed to said flexible filament independent of engagement between said crimp and said bone fixation element, whereby said crimp is fixedly positionable to said flexible filament adjacent to said proximal end of said bone fixation element so as to prevent distal movement of said flexible filament relative to said bone fixation element and hence prevent distal movement of said graft ligament in the bone tunnel.

2. An apparatus for reconstructing a ligament as in claim 1, wherein said flexible filament comprises a braided cable.

3. An apparatus for reconstructing a ligament as in claim 1, wherein the means for holding a graft ligament comprises a loop formed on the flexible filament.

4. An apparatus for reconstructing a ligament as in claim 1, further comprising a drill guide.

5. An apparatus for reconstructing a ligament as in claim 4, wherein the drill guide includes an endosteal guide.

6. An apparatus for reconstructing a ligament as in claim 1, wherein the thread comprises a helical thread encircling the bone fixation element.

7. A method for reconstructing a ligament, said method comprises:
    providing apparatus for reconstructing a ligament, said apparatus comprising:
        a bone fixation element having a distal end, a proximal end, and a central bore extending between said distal end and said proximal end, said central bore having a first diameter, said bone fixation element comprising an exterior surface with a thread outwardly projecting therefrom and said bone fixation element being adapted for positioning in a bone tunnel;
        a flexible filament having a distal end and a proximal end, said distal end having retaining means for holding a graft ligament, and said flexible filament having a second diameter smaller than said first diameter so as to allow said flexible filament to slidingly pass through said central bore of said bone fixation element, whereby said flexible filament holding the graft ligament in the bone tunnel is slideably positionable through said central bore of said bone fixation element; and
        a crimp configured for attachment to said flexible filament, said crimp having at least one given cross-sectional width, said at least one given cross-sectional width being greater than said first diameter, whereby said crimp is fixedly positionable to said flexible filament adjacent to said proximal end of said bone fixation element so as to prevent distal movement of said flexible filament relative to said bone fixation element and hence prevent distal movement of said graft ligament in the bone tunnel;
    positioning said flexible filament through said central bore of said bone fixation element, positioning said bone fixation element in a first bone tunnel portion, and positioning said graft ligament in a second bone tunnel portion by drawing said flexible filament through said bone fixation element; and
    attaching said crimp onto said flexible filament adjacent to said proximal end of said bone fixation element such that said crimp is securely fixed to said flexible filament independent of the engagement between said crimp and said bone fixation element, said crimp being attached to the flexible filament after said graft ligament is positioned within said second bone tunnel.

8. A method for reconstructing a ligament as in claim 7, further comprising attaching a graft ligament to said retaining means for holding a graft ligament.

9. A method for reconstructing a ligament as in claim 8, further comprising tensioning said flexible filament such that said crimp is biased against said bone fixation element so as to secure said graft ligament inside said bone tunnel.

10. A method for reconstructing a ligament comprising the steps of:
   forming a tunnel within a bone;
   securing a bone fixation element within the tunnel, a flexible filament extending through a bore formed on the bone fixation element so that at least a portion of the flexible filament is disposed within at least a portion of the tunnel, the bone fixation element having an outwardly projecting thread that engages the bone;
   securing a crimp onto the flexible filament at a location spaced apart from the bone fixation element such that the crimp is securely fixed to the flexible filament, said crimp being secured onto the flexible filament after the at least a portion of the flexible filament is disposed within the at least a portion of the tunnel; and
   tensioning the flexible filament such that the crimp is biased against the bone fixation element.

11. A method for reconstructing a ligament as in claim 10, wherein the step of forming a tunnel comprises drilling a first bone tunnel through at least a portion of a tibia and at least a portion of a femur, a distal end of the first bone tunnel forming an opening on the tibia.

12. A method for reconstructing a ligament as in claim 11, further comprising the step of inserting an endosteal guide through the distal end of the first bone tunnel.

13. A method for reconstructing a ligament as in claim 12, wherein the endosteal guide comprises means for gripping the flexible filament.

14. A method for reconstructing a ligament as in claim 11, further comprising drilling a second bone tunnel through a portion of the femur so as to intersect with the first bone tunnel.

15. A method for reconstructing a ligament as in claim 14, wherein the second bone tunnel intersects with the first bone tunnel at an angle.

16. A method for reconstructing a ligament as in claim 15, wherein the angle is in a range of about 30° to about 60°.

17. A method for reconstructing a ligament as in claim 14, wherein the step of securing the bone fixation element comprises securing the bone fixation element within the second bone tunnel.

18. A method for reconstructing a ligament as in claim 10, wherein the step of securing a bone fixation element within the tunnel comprises screwing the bone fixation element into the tunnel.

19. A method for reconstructing a ligament as in claim 10, wherein the step of securing the bone fixation element within the tunnel comprises:
   advancing the flexible filament through the tunnel; and
   passing the bone fixation element over the flexible filament.

20. A method for reconstructing a ligament as in claim 10, further comprising securing a ligament to the flexible filament.

* * * * *

UNITED STATES PATENT AND TRADEMARK OFFICE
CERTIFICATE OF CORRECTION

| | | |
|---|---|---|
| PATENT NO. | : 6,994,725 B1 | Page 1 of 1 |
| APPLICATION NO. | : 09/970559 | |
| DATED | : February 7, 2006 | |
| INVENTOR(S) | : E. Marlowe Goble | |

It is certified that error appears in the above-identified patent and that said Letters Patent is hereby corrected as shown below:

Column 1.Line 57 (drawing descriptions) DELETE "pars" and ADD --parts--

Signed and Sealed this

Tenth Day of April, 2007

JON W. DUDAS
*Director of the United States Patent and Trademark Office*